(12) United States Patent
Broy

(10) Patent No.: US 7,664,607 B2
(45) Date of Patent: Feb. 16, 2010

(54) PRE-CALIBRATED GAS SENSOR

(75) Inventor: Stephen H. Broy, Riverside, CA (US)

(73) Assignee: Teledyne Technologies Incorporated, Los Angeles, CA (US)

( * ) Notice: Subject to any disclaimer, the term of this patent is extended or adjusted under 35 U.S.C. 154(b) by 0 days.

(21) Appl. No.: 11/243,042

(22) Filed: Oct. 4, 2005

(65) Prior Publication Data
US 2007/0078608 A1    Apr. 5, 2007

(51) Int. Cl.
*G01N 7/00* (2006.01)

(52) U.S. Cl. ......................................................... 702/24

(58) Field of Classification Search .................. 702/24; 73/53.01, 23.2
See application file for complete search history.

(56) References Cited

U.S. PATENT DOCUMENTS

| | | |
|---|---|---|
| 2,752,308 A | 6/1956 | Andrus |
| 2,805,191 A | 9/1957 | Hersch |
| 2,913,511 A | 11/1959 | Grubb |
| 2,992,170 A | 7/1961 | Robinson |
| 3,124,520 A | 3/1964 | Juda |
| 3,132,082 A | 5/1964 | Overmyer |
| 3,313,720 A | 4/1967 | Robinson |
| 3,316,161 A | 4/1967 | Jung et al. |
| 3,325,378 A | 6/1967 | Greene et al. |
| 3,328,277 A | 6/1967 | Solomons |
| 3,342,558 A | 9/1967 | Reinecke |
| 3,351,544 A | 11/1967 | Medlar |
| 3,410,778 A | 11/1968 | Krasberg |
| 3,429,796 A | 2/1969 | Lauer |
| 3,437,542 A | 4/1969 | Mills |
| 3,438,872 A | 4/1969 | Johansson |
| 3,454,485 A | 7/1969 | Hauk et al. |
| 3,503,861 A | 3/1970 | Volpe |
| 3,510,421 A | 5/1970 | Gealt |
| 3,577,332 A | 5/1971 | Porter et al. |
| 3,767,552 A | 10/1973 | Lauer |
| 3,776,832 A | 12/1973 | Oswin et al. |
| 3,792,275 A | 2/1974 | Leftwich et al. |
| 3,797,942 A | 3/1974 | Joly |
| 3,798,750 A | 3/1974 | Niedrach |
| 3,829,693 A | 8/1974 | Schwarz |

(Continued)

FOREIGN PATENT DOCUMENTS

CH    560390    3/1975

(Continued)

OTHER PUBLICATIONS http://en.wikipedia.org/wiki/Operational_amplifier, p. 1-11.*

(Continued)

*Primary Examiner*—Tung S Lau
(74) *Attorney, Agent, or Firm*—K&L Gates LLP

(57) ABSTRACT

A pre-calibrated gas sensor is disclosed. The gas sensor includes a cathode and an anode for outputting a current signal responsive to a sensed oxygen concentration and a signal processing module in communication with the cathode and the anode and configured to receive the current signal and to output a pre-calibrated signal representative of the sensed gas concentration based on a value of the received current signal.

14 Claims, 5 Drawing Sheets

U.S. PATENT DOCUMENTS

| | | | |
|---|---|---|---|
| 3,929,587 A | 12/1975 | Gallagher | |
| 3,932,754 A | 1/1976 | Riedl et al. | |
| 3,989,614 A | 11/1976 | Tien | |
| 3,997,786 A | 12/1976 | Lauer et al. | |
| 4,017,950 A | 4/1977 | Schultz | |
| 4,025,412 A | 5/1977 | La Conti | |
| 4,044,193 A | 8/1977 | Petrow et al. | |
| 4,069,420 A | 1/1978 | Ross | |
| 4,077,861 A | 3/1978 | Lauer | |
| 4,151,503 A | 4/1979 | Cermak et al. | |
| 4,152,233 A | 5/1979 | Chand | |
| 4,182,666 A | 1/1980 | Dickinson et al. | |
| 4,206,647 A | 6/1980 | Merchant et al. | |
| 4,208,786 A | 6/1980 | Merchant et al. | |
| 4,222,006 A | 9/1980 | Schneider | |
| 4,228,352 A | 10/1980 | Adrian | |
| 4,253,931 A | 3/1981 | Gold et al. | |
| 4,268,370 A | 5/1981 | Radhakrishna | |
| 4,288,544 A | 9/1981 | Suzuki et al. | |
| 4,324,256 A | 4/1982 | Vesterager | |
| 4,326,927 A | 4/1982 | Stetter et al. | |
| 4,345,985 A | 8/1982 | Tohda et al. | |
| 4,355,234 A | 10/1982 | Fertig et al. | |
| 4,367,133 A | 1/1983 | Lauer et al. | |
| 4,391,691 A * | 7/1983 | Linder et al. | 204/408 |
| 4,420,687 A | 12/1983 | Martinez et al. | |
| 4,435,268 A | 3/1984 | Martin et al. | |
| 4,466,878 A | 8/1984 | DiNitto et al. | |
| 4,471,942 A | 9/1984 | Kocanowski | |
| 4,477,316 A | 10/1984 | Sakai et al. | |
| 4,495,051 A | 1/1985 | Fujita et al. | |
| 4,508,598 A | 4/1985 | Giner | |
| 4,514,635 A | 4/1985 | Ishida et al. | |
| 4,533,456 A | 8/1985 | Kratochvil et al. | |
| 4,534,356 A | 8/1985 | Papadakis | |
| 4,558,342 A | 12/1985 | Sclar | |
| 4,609,452 A * | 9/1986 | Shimomura | 204/425 |
| 4,647,359 A | 3/1987 | Lindstrom | |
| 4,655,892 A | 4/1987 | Satta et al. | |
| 4,667,105 A | 5/1987 | Miyatake et al. | |
| 4,668,374 A | 5/1987 | Bhagat et al. | |
| 4,695,361 A | 9/1987 | Grady et al. | |
| 4,718,991 A | 1/1988 | Yamazoe et al. | |
| 4,729,824 A | 3/1988 | Giner | |
| 4,772,790 A | 9/1988 | Aldridge | |
| 4,776,942 A | 10/1988 | Neti et al. | |
| 4,795,533 A | 1/1989 | Young et al. | |
| 4,820,386 A | 4/1989 | LaConti et al. | |
| 4,828,941 A | 5/1989 | Sterzel | |
| 4,861,454 A | 8/1989 | Ushizawa et al. | |
| 4,870,855 A | 10/1989 | Shafer | |
| 4,874,500 A | 10/1989 | Madou et al. | |
| 4,880,519 A | 11/1989 | Wang et al. | |
| 4,897,174 A | 1/1990 | Wang et al. | |
| 4,900,422 A * | 2/1990 | Bryan et al. | 204/401 |
| 4,914,719 A | 4/1990 | Conlon et al. | |
| 4,948,496 A | 8/1990 | Chand | |
| 4,959,138 A | 9/1990 | Brinkmann et al. | |
| 4,960,497 A | 10/1990 | Gallagher | |
| 5,013,920 A | 5/1991 | Asano et al. | |
| 5,034,595 A | 7/1991 | Grendys | |
| 5,065,025 A | 11/1991 | Doyle | |
| 5,070,244 A | 12/1991 | Simpson | |
| 5,071,526 A | 12/1991 | Pletcher et al. | |
| 5,083,304 A | 1/1992 | Cahill | |
| 5,085,759 A | 2/1992 | Harker | |
| 5,085,760 A | 2/1992 | Razaq et al. | |
| 5,095,193 A | 3/1992 | Doyle | |
| 5,102,525 A | 4/1992 | Miyahara et al. | |
| 5,126,035 A | 6/1992 | Kiesele et al. | |
| 5,163,332 A | 11/1992 | Wong | |
| 5,164,053 A | 11/1992 | Razaq et al. | |
| 5,166,892 A | 11/1992 | Inoue et al. | |
| 5,183,549 A | 2/1993 | Joseph et al. | |
| 5,207,087 A | 5/1993 | Costello | |
| 5,215,644 A | 6/1993 | Ashikaga | |
| 5,222,389 A | 6/1993 | Wong | |
| 5,237,855 A | 8/1993 | Gates | |
| 5,256,273 A | 10/1993 | Gallagher et al. | |
| 5,263,361 A | 11/1993 | Gates | |
| 5,276,615 A | 1/1994 | Tournier et al. | |
| 5,284,566 A | 2/1994 | Cuomo et al. | |
| 5,310,610 A | 5/1994 | Furubayashi et al. | |
| 5,326,447 A | 7/1994 | Fletcher | |
| 5,332,901 A | 7/1994 | Eckles et al. | |
| 5,344,626 A | 9/1994 | Abler | |
| 5,346,470 A | 9/1994 | Hobbs et al. | |
| 5,382,331 A | 1/1995 | Banks | |
| 5,393,392 A | 2/1995 | Masi | |
| 5,395,507 A | 3/1995 | Aston et al. | |
| 5,425,868 A | 6/1995 | Pedersen | |
| 5,429,105 A * | 7/1995 | Bennett et al. | 123/693 |
| 5,433,764 A | 7/1995 | Matschke | |
| 5,440,477 A | 8/1995 | Rohrberg et al. | |
| 5,453,172 A | 9/1995 | Alberti et al. | |
| 5,466,350 A | 11/1995 | Baker et al. | |
| 5,494,068 A | 2/1996 | Schuster | |
| 5,535,614 A | 7/1996 | Okamoto et al. | |
| 5,556,533 A | 9/1996 | Nozoe et al. | |
| 5,583,635 A | 12/1996 | Miura et al. | |
| 5,642,722 A | 7/1997 | Schumacher et al. | |
| 5,644,068 A | 7/1997 | Okamoto et al. | |
| 5,668,302 A | 9/1997 | Finbow et al. | |
| 5,687,758 A | 11/1997 | Schuster | |
| 5,689,114 A | 11/1997 | Miyazaki et al. | |
| 5,690,808 A | 11/1997 | Akmal et al. | |
| 5,691,464 A | 11/1997 | Cao | |
| 5,714,046 A | 2/1998 | Lauer et al. | |
| 5,728,289 A | 3/1998 | Kirchnavy et al. | |
| 5,764,067 A | 6/1998 | Rastegar | |
| 5,788,832 A | 8/1998 | Howard et al. | |
| 5,837,454 A | 11/1998 | Cozzette et al. | |
| 5,883,009 A | 3/1999 | Villa et al. | |
| 5,889,199 A | 3/1999 | Wong et al. | |
| 5,944,969 A | 8/1999 | Scheffler et al. | |
| 5,969,223 A | 10/1999 | Nagai et al. | |
| 5,985,129 A | 11/1999 | Gough et al. | |
| 5,992,463 A | 11/1999 | Redemann et al. | |
| 5,996,337 A * | 12/1999 | Blosser et al. | 60/274 |
| 6,019,879 A | 2/2000 | Chu et al. | |
| 6,024,853 A | 2/2000 | Kiesele et al. | |
| 6,096,186 A | 8/2000 | Warburton | |
| 6,176,989 B1 | 1/2001 | Shi | |
| 6,201,245 B1 | 3/2001 | Schrader | |
| 6,265,750 B1 | 7/2001 | Feng et al. | |
| 6,284,545 B1 | 9/2001 | Warburton et al. | |
| 6,287,519 B1 | 9/2001 | Nordman et al. | |
| 6,454,921 B1 | 9/2002 | Hodges et al. | |
| 6,524,740 B1 * | 2/2003 | Broy et al. | 429/61 |
| 6,565,509 B1 | 5/2003 | Say et al. | |
| 6,604,405 B2 | 8/2003 | Whynall et al. | |
| 6,773,577 B1 | 8/2004 | Broy et al. | |
| 6,832,072 B2 | 12/2004 | Hobbs et al. | |
| 6,840,084 B2 | 1/2005 | Nikolskaya | |
| 2002/0097396 A1 | 7/2002 | Schafer | |
| 2003/0028354 A1 | 2/2003 | Elwood et al. | |
| 2003/0029721 A1 | 2/2003 | Broy et al. | |
| 2003/0155240 A1 | 8/2003 | Ulkem | |
| 2003/0209140 A1 * | 11/2003 | Kutt et al. | 95/8 |
| 2004/0140211 A1 | 7/2004 | Broy et al. | |
| 2005/0098447 A1 | 5/2005 | Broy et al. | |
| 2006/0107774 A1 | 5/2006 | Meyberg | |
| 2006/0243603 A1 | 11/2006 | Jiang et al. | |
| 2006/0249383 A1 | 11/2006 | Broy et al. | |

| | | |
|---|---|---|
| 2008/0274401 A1 | 11/2008 | Broy et al. |

FOREIGN PATENT DOCUMENTS

| | | |
|---|---|---|
| DE | 1254007 | 11/1967 |
| DE | 01330704 B3 | 12/2004 |
| EP | 0113966 | 7/1984 |
| EP | 0122511 | 10/1984 |
| EP | 0180138 A2 | 5/1986 |
| EP | 0470473 A1 | 2/1992 |
| EP | 0777121 A2 | 11/2004 |
| FR | 1057663 | 3/1954 |
| GB | 969607 | 9/1964 |
| GB | 969608 | 9/1964 |
| GB | 1092909 | 11/1967 |
| GB | 1166683 | 8/1969 |
| GB | 2267348 A | 1/1993 |
| GB | 2262338 A | 6/1993 |
| GB | 2284059 A | 5/1995 |
| GB | 2320962 | 7/1998 |
| GB | 2327125 | 1/1999 |
| GB | 2392727 | 3/2004 |
| JP | 54091536 | 7/1979 |
| JP | 59003345 A | 6/1982 |
| JP | 58109875 A | 6/1983 |
| JP | 59054936 A | 3/1984 |
| JP | 61267274 A | 5/1985 |
| JP | 2027254 A | 6/1988 |
| JP | 1186764 A | 7/1989 |
| JP | 03-148060 | 6/1991 |
| JP | 3273135 A | 12/1991 |
| JP | 3273235 | 12/1991 |
| JP | 4167087 A | 6/1992 |
| JP | 6148069 A | 5/1994 |
| JP | 06-213861 | 8/1994 |
| JP | 06-222038 | 8/1994 |
| JP | 8233770 A | 9/1996 |
| JP | 2001-258165 A | 9/2001 |
| NL | 6610435 | 1/1968 |
| WO | WO 87/02461 | 4/1997 |

OTHER PUBLICATIONS http://mw1.merriam-webster.com/dictionary/electrolyte, p. 1.*
http://mw1.merriam-webster.com/dictionary/solution, p. 1.*
No Publication date, 37 CFR 1.97, 1.98 and MPEP § 609.
"Fuel Cells," a Review of Government Sponsored Reserarch, 1950-1964 NASA SP 1210, pp. 26 and 27.
Projects - Two Line Mini-Terminal, http://www.ezi.com/-rsch/projects.htm, pp. 1-3, accessed Mar. 16, 2009.
http://mw1.merriam-webster.com/dictionary/solution, pp. 1-2, accessed Mar. 25, 2009.
http://mw1.merriam-webster.com/dictionary/electrolyte, p. 1, accessed Mar. 25, 2009.
http://en.wikipedia.org/wiki/Operational_amplifier, pp. 1-11, accessed Feb. 27, 2007.
Spec. Control Drawing, Micro Fuel Cell, Class B2C, drawing No. A-66797 available at http://www.teledyne-ai.com/pdf/schem_a66797.pdf on Feb. 25, 2005.
Outline Diagram, Cell Block Assy, Trace Oxygen Analyzer, drawing No. C-64666, available at http://www.teledyne-ai.com/pdf/schem_c64666.pdf on Feb. 25, 2005.
Operating Instructions for Model 3290 Percent Oxygen Analyzer, copyright 1999 Teledyne Analytical Instruments, available at http://vvww.teledyne-ai.com/manuals/man_3290.pdf on Feb. 25, 2005.
Operating Instructions for Insta-Trans Trace and Percent Oxygen Transmitter, copyright 2000 Teledyne Analytical Instruments, available at http://www.teledyne-ai.com/manuals/man_instatrans.pdf on Feb. 25, 2005.
Model OXYMASTER 16T Process Trace Oxygen Analyzer, available at http://www.pro-chem-analytik.de/Oxymaster16Tenglish.html on Apr. 23, 2005.
Model 3290 AL Oxygen Analyzer, Final Assembly, drawing No. C-65676; available at http://www.teledyne-ai.com/pdf/schem_c65676.pdf on Feb. 25, 2005.
"R-17MED Oxygen Sensor," Specification Sheet, 2005, Teledyne Analytical Instruments, 1 page.
Low cost high performance seismic a/d converter, Digitizers, available at http://mariottim.interfree.it/dox04 e. htm, di Mauro, Mariotti, pp. 1-9, accessed Mar. 16, 2009.
"Modular Component Interfaces for Surface-Mount Fluid Distribution Components - Part 1: Elastomeric Seals," ANSI/ISA - 76.00.02, North Carolina, 2002, pp. 1-11.
Tatera, Jim, et al., PowerPoint presentation entitled "NeSSI - New Sampling/Sensor Initiative - Interface to the Process," Fall Sponsor Meeting, Center for Process Analytical Chemistry, Nov. 5, 2001, 12 pages.
Operating Instructions for Model OT-3 Trace Oxygen Analyzer, copyright 2000 Teledyne Analytical Instruments; available at http://www.teledyne-ai.com/manuals/man_ot-3.pdf.
The Basics - Sensors, at http://www.seattlerobotics.org/encoder/jul97/basics.html, Aug. 12, 2003, pp. 1-6, accessed Mar. 16, 2009.
The Basics - Microcontrollers, (part 1) at basics,http://www.seattlerobotics.org/encoder/sep97/basics.html, pp. 1-6, accessed Mar. 16, 2009.
"Gel-Silica Science" by L.L. Hench & W. Vasconceles in the Annual Review Material Science, 1990, vol. 20, pp. 269-298.
A.J. Polak et al., Sensors and Actuators 9, pp. 1-7, 1986.
"Development of Small Polymer Fuel Cell," Watkins et al., Proceedings of 32nd Power Series Conference, Cherry Hill, N.J., Jun. 9-12 1986, The Electrochemical Society, pp. 590-595.
Szeles, Donald M., "Variations in Calibration of Radiometers Using Cut-on Optical Filters," Application Brief 5, Jul. 1978, Dexter Research Center (updated Nov. 2004).
Szeles, Donald M., "Blackbody Calculations Using a Programmable Calculator," Application Brief 4, Jul. 1978, Dexter Research Center (updated Aug. 2002).
Szeles, Donald M., "Emissivity Correction for a Radiometer," Application Brief 3, Jul. 1978, Dexter Research Center (updated Mar. 2003).
Szeles, Donald M., "Temperature Compensation of DC Radiometer," Application Brief 2, Jul. 1978, Dexter Research Center (updated Sept. 2002).
Szeles, Donald M., "A Simple DC Radiometer," Application Brief 1, Jul. 1978, Dexter Research Center (updated Dec. 2006).
"The Oxide Handbook" edited by G. V. Samsonov, 1973, pp. 266-274.
R.P. Hamlen et al., "Immobilized Phosphoric Acid Intermediate Temperature Fuel Cell", Electrochemical Technology, vol. 4 (No. 3-4), pp. 172-174, Mar. - Apr. 1966.
Ives, et al., "Reference Electrodes", 1961, pp. 333-334.

* cited by examiner

PRE-CALIBRATED GAS SENSOR

CROSS-REFERENCE TO RELATED APPLICATIONS

Not Applicable

STATEMENT REGARDING FEDERALLY SPONSORED RESEARCH OR DEVELOPMENT

Not Applicable

NAMES OF THE PARTIES TO A JOINT RESEARCH AGREEMENT

Not Applicable

REFERENCE TO A SEQUENCE LISTING

Not Applicable

TECHNICAL FIELD OF THE INVENTION

The present invention relates generally to a gas sensor, and more particularly, to a pre-calibrated oxygen sensor.

BACKGROUND OF THE INVENTION

FIG. 1 illustrates a cross-sectional view of a conventional oxygen sensor 310 such as, for example, a model B-2C oxygen sensor sold by Teledyne Analytical Instruments, City of Industry, Calif. The oxygen sensor 310 consists of a cathode 302 and an anode 304 sealed in a housing 306 filled with an appropriate electrolyte solution. Oxygen diffuses into the interior of the sensor housing 306 through a thin sensing membrane 308. A flexible expansion membrane 312 at the opposite end of the oxygen sensor 310 permits expansion and contraction of the electrolyte volume. The sensing membrane 308 is sealed in place by means of press fit or heat seal. The expansion membrane 312 is sealed in place by means of heat or mechanical seal. Reduction of oxygen at the cathode 302 causes an ionic current to flow from the cathode 302 to the anode 304 through an externally-connected sensing circuit (not shown).

Present demands on oxygen analyzers require that the oxygen sensors that they employ, such as the model B-2C oxygen sensor described above, effectively and continuously measure the concentration of oxygen within an incoming gas stream. For example, some trace oxygen monitoring systems require the near continuous measurement of oxygen in a gaseous stream in amounts at or below several hundred parts per million (PPM). Other percent-level oxygen sensors measure much higher levels of oxygen content. Regardless of the type of oxygen sensor employed, the oxygen sensor must be extremely sensitive in order to provide an accurate oxygen content indication.

As illustrated in FIGS. 2 and 3, in some prior art oxygen sensors, a clamp portion 325 engages the oxygen sensor 310 to seal the electrolyte solution in the interior of the housing 306 so that the oxygen sensor 310 may be oriented within a cavity portion of a cell block 330. A cap portion 335 of the cell block 330 is configured to engage the cavity portion such that the oxygen sensor 310 is sealably encapsulated therein. The cell block 330 may comprise a gas inlet and a gas outlet for receiving and exhausting, respectively, a sample gas stream. The cell block 330 may further comprise a hermetic electrical connection 340 for interfacing the external sensing circuit to the cathode 302 and anode 304, and to any other electrical terminals of the oxygen sensor 310. As the oxygen sensor 310 measures the oxygen concentration of the sample gas stream, the anode 304, typically formed of lead, is consumed at a rate dictated by the exposure of the sensor 310 to oxygen.

Prior to its use in a gas sensing application, it is typically necessary to calibrate the oxygen sensor 310 at the point of use by exposing of the oxygen sensor 310 to one or more calibration gases of known oxygen concentration in order to determine its current output as a function of sensed oxygen concentration. For example, the oxygen sensor 310 may be separately exposed to a "span" gas having a substantially non-zero oxygen concentration (e.g., 100 PPM) and a "zero" gas having an oxygen concentration of zero, or substantially zero. The resulting values of current output by the oxygen sensor 310 may be determined by the sensing circuit and, along with the corresponding oxygen concentrations of the span and zero gases, stored therein. Because the current output varies linearly as a function of the sensed oxygen concentration, the stored span and zero oxygen concentration values and their corresponding stored current values may be used to derive a transfer function for the oxygen sensor 310 of the form $O_2$ Conc.$=G*i_s+b$, where G represents the gain of the oxygen sensor 310 in units of oxygen concentration per unit current (e.g., PPM/μA), $i_s$ represents the current output of the oxygen sensor 310 typically expressed in units of μA, and b represents the zero-offset of the oxygen sensor 310 in units of oxygen concentration (e.g., PPM). Accordingly, the external sensing circuit may apply the transfer function to determined values of the oxygen sensor's 310 current output to determine the corresponding values of oxygen concentration.

One problem associated with the calibration of the oxygen sensor 310 at the point of use is the need to procure and maintain a supply of span and zero gases. This need not only increases the expense of the oxygen sensing application in terms of material and labor costs, but also necessitates the exposure of field personnel to hazards associated with the handling of highly pressurized containers in which calibration gases are typically stored.

Another problem relating to the calibration of the oxygen sensor 310 at the point of use arises from the gradual lessening of the oxygen sensor's 310 gain G over time. Termed "drift," this decrease is caused by a reduction in the ion concentration of the electrolyte solution and the formation of anode precipitates, both of which naturally occur during operation of the oxygen sensor 310. It is thus typically necessary to calibrate the oxygen sensor 310 periodically throughout its operating lifetime in order to "reset" the value of the gain G so that accurate oxygen concentration measurements may be continually obtained. The necessity of periodic calibration further increases operational expenses and hazards associated with the oxygen sensing application.

Accordingly, there exists a need for an improved oxygen sensor that is pre-calibrated at a location other than the point of use and configured such that the effects of sensor drift are minimized.

BRIEF SUMMARY OF THE INVENTION

This application discloses a pre-calibrated gas sensor including a cathode and an anode for outputting a current signal responsive to a sensed oxygen concentration. The gas sensor further includes a signal processing module in communication with the cathode and the anode. The signal processing module is configured to receive the current signal and to output a pre-calibrated signal representative of the sensed gas concentration based on a value of the received current signal.

This application further discloses a system for pre-calibrating a gas sensor. According to various embodiments, the system includes a cathode and an anode for outputting a first current signal responsive to a sensed oxygen concentration in a first gas, and a signal processing module in communication with the cathode and the anode. The signal processing module is configured to receive the first current signal and to output a first digital code representative of the first current signal. The system further includes a host in communication with the signal processing module. The host is configured to receive the first digital code and to determine a pre-calibration transfer function based thereon.

This application further discloses a method for pre-calibrating a gas sensor. According to various embodiments, the method includes determining a pre-calibration transfer function and communicating the pre-calibration transfer function to the gas sensor for storage therein.

Unless otherwise indicated, all numbers expressing a size, quantity, and so forth used in the present specification and claims are to be understood as being modified in all instances by the term "about." Accordingly, unless indicated to the contrary, the numerical parameters set forth in the following specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, may inherently contain certain errors necessarily resulting from the standard deviation found in their respective testing measurements.

The reader will appreciate the foregoing details and advantages of the present invention, as well as others, upon consideration of the following detailed description of embodiments of the invention. The reader also may comprehend such additional details and advantages of the present invention upon making and/or using embodiments within the present invention.

DESCRIPTION OF THE FIGURES

Various embodiments of the invention will be described by way of example in conjunction with the following figures, wherein.

DETAILED DESCRIPTION OF THE INVENTION

Figure 1:
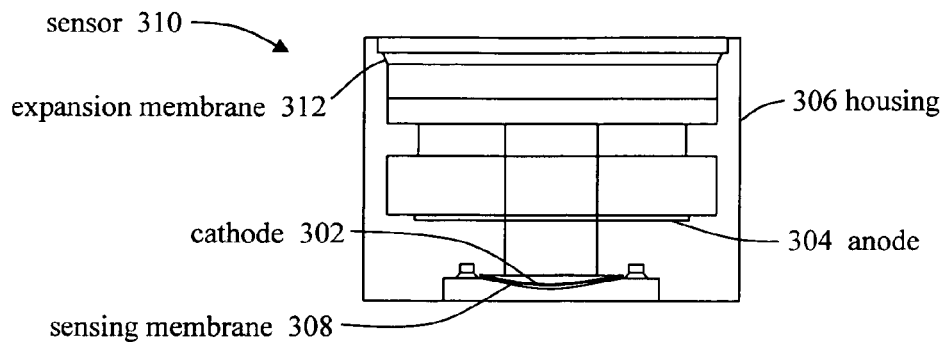
FIG. 1 illustrates a cross-sectional view of a conventional oxygen sensor.

In the present detailed description of the invention, the invention will be illustrated in the form of a gas sensor adapted for use as a sealed galvanic oxygen sensor. It will be understood, however, that the invention is not limited to embodiment in such form and may have application in any gas sensor. For example, the gas sensor may be in the form of a trace oxygen sensor configured for use within in a cell block. Alternatively, the gas sensor may be in the form of a trace oxygen sensor or a percent oxygen sensor configured for use without a cell block. Thus, while the present invention is capable of embodiment in many different forms, for ease of description this detailed description and the accompanying drawings disclose only specific forms as examples of the invention. Those having ordinary skill in the relevant art will be able to adapt the invention to application in other forms not specifically presented herein based upon the present description.

Also, for ease of description, the invention and devices to which it may be attached may be described and/or illustrated herein in a normal operating position, and terms such as upper, lower, front, back, horizontal, proximal, distal, etc., may be used with reference to the normal operating position of the referenced device or element. It will be understood, however, that the apparatus of the invention may be manufactured, stored, transported, used, and sold in orientations other than those described and/or illustrated.

Other than in the operating examples, or unless otherwise expressly specified, all of the numerical ranges, amounts, values and percentages such as those for amounts of materials, and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In addition, for ease of description, the terms "anode" and "cathode" are used herein to refer to the electrodes of the present invention. It will be understood that the terms "anode" and "cathode" are used herein to refer, generally, to the electrodes of the present invention and, in particular, are used to refer to electrodes that may be incorporated as components of an oxygen sensor. It will be understood that the invention has applicability to gas sensors including electrodes identified as other than anodes and cathodes. For example, as is known in the art, other types of gas sensors may incorporate electrodes in the forms of a "sensing" or "working" electrode (the cathode) and a counter electrode (the anode), as well as reference electrode(s). The terms "anode" and "cathode", as used herein, are intended to include these other types of electrodes.

A typical galvanic oxygen sensor consists, in part, of a machined plastic body filled with an electrolyte solution, a cathode (working electrode) manufactured from perforated sheet metal such as brass and plated with an appropriate noble metal such as, for example, rhodium, gold, or silver, and an anode (counter electrode) formed of any anode material such as, for example, compressed lead pellets. The electrolyte solution may be, for example, a potassium hydroxide solution. A gaseous stream enters the body by diffusing through a synthetic membrane positioned at an inlet and is transported through a thin electrolyte layer to the cathode. The oxygen is reduced to hydroxyl ions at the cathode. Simultaneously, anode material, such as lead, is continually oxidized at the anode. Thus, the following electrochemical reactions occur at the cathode and the lead anode:

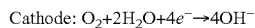
Cathode: $O_2 + 2H_2O + 4e^- \rightarrow 4OH^-$

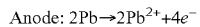
Anode: $2Pb \rightarrow 2Pb^{2+} + 4e^-$

Lead oxide formed, though soluble in the electrolyte solution initially, will eventually deposit on the lead anode as the electrolyte becomes saturated with lead ions. When the cathode and the anode are electrically connected to a circuit, an ionic current flows through the sensor. The ionic current is proportional to the rate of oxygen consumption. In embodiments of the present invention, the ionic current generated by the oxygen sensor is received by an electronic device integral to the oxygen sensor, such as a signal processing module described hereinbelow. A connection between the electronic device and the cathode may be achieved by welding a small diameter (typically 0.01 inch) silver wire to the cathode. A connection between the electronic device and the anode may be achieved by compressing (sintering) lead pellets around a small coil of nickel wire in an attempt to maximize the contact surface area between the wire and the lead particles.

Figure 4A:
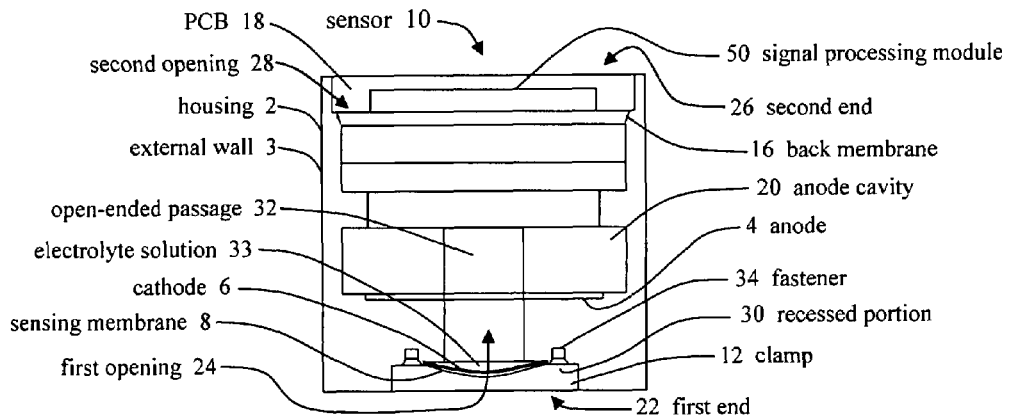
FIG. 4a illustrates a cross-sectional view of an oxygen sensor, according to various embodiments of the present invention.

Referring now to the drawings, which are for the purpose of illustrating embodiments of the invention and not for the purpose of limiting the same, FIG. 4a depicts a cross-sectional view of a gas sensor constructed according to various embodiments of the present invention and in the form of an oxygen sensor 10. As will be apparent from the following description, embodiments of the oxygen sensor 10 improve upon the construction of known gas sensors with respect to at least the ability of the oxygen sensor 10 to output a calibrated and/or drift-compensated signal representative of a sensed oxygen concentration without the need for calibrating the oxygen sensor 10 at the point of use. The oxygen sensor 10 may include a housing 2, an anode 4, a cathode 6, a sensing membrane 8, a clamp 12, a signal processing module 50, an expansion or back membrane 16, and a printed circuit board 18.

The housing 2 may be an open-ended cylinder that comprises an anode cavity 20 defined by an internal wall of the housing 2. The housing 2 may be a single formed component or may be separately formed components that are secured together by any known method such as, for example, heat sealing, welding, or press fit. All components that form the housing 2 may be formed separately or as a single unit through processes such as, for example, pouring or injection molding. The housing 2 may be fabricated from, for example, any resilient insulating material, including, for example, a thermoplastic material such as, for example, polyethylene. The housing 2 may be any shape or configuration, such as, for example, a cylindrical body with the internal and external walls being generally coaxial, as illustrated. The housing 2 may have any suitable dimensions. For example, as incorporated in oxygen sensor 10, the housing 2 may have a longitudinal length of 1.25 inches and a diameter of 1.2 inches. Other housing dimensions will follow from the application for which the sensor 10 is adapted.

The housing 2 may include a first end 22 defining a first opening 24 and a second end 26 defining a second opening 28. The first opening 24 receives the entering stream of gas to be sensed. The first opening 24 may be any size or shape suitable for receiving the gaseous stream. For example, the opening 24 may have a circular cross section and have a diameter of 0.9 inches. As illustrated, the first opening 24 may be located within a recessed portion 30 of the first end 22 and may be centrally spaced relative to the external wall 3 of the housing 2. The recessed portion 30 may be any size and geometry, such as, for example, a cylindrical cavity having a diameter of 0.7 inches that is centrally spaced from the external wall 3 of the housing 2. The height of the recessed portion 30 may be substantially equal to the total thickness of the clamp 12, described herein, so that an outer surface of the clamp 12 may be substantially flush with an inner edge of the housing 2 after being placed within the recessed portion 30 of the housing 2 and secured thereto.

The second opening 28 of the housing 2 may be positioned opposite the first opening 24 and may be defined by the external wall 3 of the housing 2. The second opening 28 may be any size or geometry suitable for receiving the back membrane 16 and printed circuit board 18, such as, for example, a circular cross section having a diameter of 1.0 inch that is centrally positioned relative to the external wall 3 of the housing 2. The height of the second opening 28 may be substantially equal to the total thickness of the back membrane 16 and the printed circuit board 18 so that a surface of the printed circuit board 18 may be substantially flush with an edge of the housing 2 after being placed over the back membrane 16 and sealed thereto to complete the back portion of the sensor 10.

The internal wall of the housing 2 defines an open ended passage 32 that extends into the housing 2 to form the anode cavity 20, thereby providing fluid communication to the electrolyte 33 in the anode cavity 20 for the gases entering the first opening 24. The length of the internal wall may define the passage 32 and may have any suitable longitudinal length. In one embodiment, the longitudinal length of the internal wall is 0.9 inches. It will be understood that the anode cavity 20 may be any chamber defined by the interior dimensions of the housing 2. The anode cavity 20 may be any suitable size and geometry known in the art for containing an amount of electrolyte 33 sufficient for the effective measurement of the entering gaseous stream.

The anode 4 may be formed of any electrically conductive anode material, such as, for example, lead. As adapted for use in the oxygen sensor 10, the anode 4 may be a solid lead body formed of sintered lead pellets, or may be in the form of a lead wire. The anode 4 may be positioned in the anode cavity 20 in any known manner, such as for example, over or around the internal wall that forms the passage 32 that leads to the anode cavity 20. It will be understood that the anode 4 may be fabricated in a variety of ways, such as, for example, by stamping a flat pattern from a sheet of an electrically conductive metal.

The cathode 6 may be a concave disc-like member formed of any cathode material known in the art. The cathode 6 may be constructed of, for example, a noble metal such as silver, or a substrate plated with, for example, silver or rhodium. As provided in sensor 10, the cathode 6 may include a concave base having a diameter of 0.9 inches and thickness of 0.01 inches. The cathode base may include a curved contact surface that may be, for example, concave relative to the anode cavity 20 when assembled, and that includes a number of small, perforated holes therethrough (not shown). Although those skilled in the art may, upon considering the present disclosure, readily appreciate numerous ways to form the cathode 6, the cathode 6 may be manufactured by photochemically etching a flat pattern of the cathode 6 from a sheet of any suitable material, such as, for example, nickel or brass. The cathode 6 may then be shaped to include a concave surface, as illustrated, by using one or more of a variety of methods including, for example, the use of a progressive die. The cathode 6 may then be plated with an appropriate cathode material, such as, for example, rhodium, gold or silver.

The sensing membrane 8 may be positioned adjacent to and in contact with the cathode 6, as illustrated. The sensing membrane 8 may be constructed of any of the various types of hydrophobic, gas permeable materials known in the art. For example, as incorporated in sensor 10, the sensing membrane 8 may be formed of a Teflon® film. The permeability of the material is such that gas may pass therethrough, but electrolyte 33 solution will not.

The second opening 28 may be sealed with a back membrane 16 that allows for expansion or contraction of the electrolyte 33 volume. The back membrane 16 may be any suitable resilient material, such as a thermoplastic, including polyethylene. The back membrane 16 may be sealed to the housing 2 by any means known in the art, but in sensor 10 the back membrane 16 may be thermally sealed to the housing 6.

When present, the clamp 12 may be any clamp known to those skilled in the art for effectively retaining the cathode 6 and the sensing membrane 8 in close association with each other and together to provide a positive seal at the first opening 24 of the housing 2. The clamp 12 may be concave relative to the first opening 24 and may include a central woven mesh portion as known in the art that protects the cathode 6. The clamp 12 may be sized for receipt in the recessed portion 30 of the first end 22 and secured therein by any engagement means known in the art. For example, as incorporated into sensor 10, the clamp 12 may be fastened over the first opening 24, the cathode 6, and the sensing membrane 8 by threaded fasteners 34. The positive locking action achieved by the fasteners 34 provides the pressure required to effectively seal the sensing membrane 8 to the housing 2 over the first opening 24. The clamp 12 may be constructed of, for example, an elastomer or thermoplastic material that produces sufficient pressure against the sensing membrane 8 and housing 2 to create an effective seal.

The oxygen sensor 10 of the present invention may further include a signal processing module 50 in communication with the anode 4 and the cathode 6 and configured to provide a conductive path therebetween, thus enabling the flow of ionic current through the oxygen sensor 10 when exposed to oxygen. The anode 4 may be electrically connected to signal processing module 50 by, for example, compressed (sintered) pellets around a small coil of silver wire. The cathode 6 may be electrically connected to the signal processing module 50 by, for example, welding a small diameter (typically 0.01 inch) silver wire to the cathode 6. The signal processing module 50 may further be configured to receive the resulting current output by the oxygen sensor 10 and to output a calibrated and/or drift-compensated signal representative of a sensed oxygen concentration based on a value of the received current, as described hereinbelow. The signal processing module 50 may be positioned at any location suitable for receiving the current output by the oxygen sensor 10. As shown in FIG. 4a, for example, the signal processing module 50 may be positioned inside the oxygen sensor housing 2, and may, but need not, be positioned on the printed circuit board 18, as illustrated.

According to various embodiments and as shown in FIG. 4a, the oxygen sensor 10 may be configured for use within a cell block similar to the cell block 330 described above in connection with FIG. 3. According to such embodiments, the circuit board 18 may comprise metallic contacts (not shown) electrically connected to the signal processing module 50 and configured to interface with a hermetic electrical connection of the cell block when the oxygen sensor 10 is placed therein. Signals may thus be communicated between the signal processing module 50 and one or more circuits exterior to the cell block when the oxygen sensor 10 is sealably encapsulated therein.

Figure 4B:
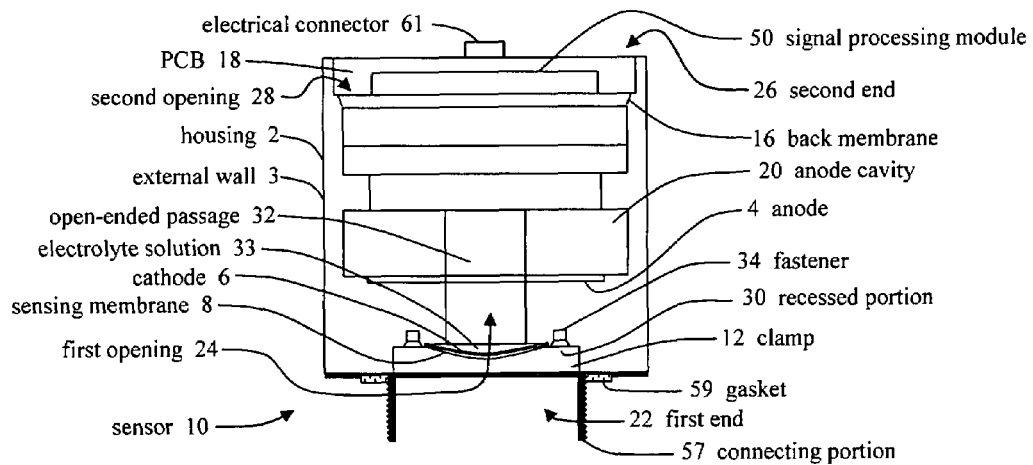
FIG. 4b illustrates a cross-sectional view of an oxygen sensor, according to various embodiments of the present invention.

According to various embodiments, the oxygen sensor 10 may be configured for use without a cell block. For example, as shown in FIG. 4b, the oxygen sensor 10 may comprise a connecting portion 57 configured for removable engagement by a connecting-type sensor holder (not shown). The oxygen sensor 10 may further comprise a gasket 59 for providing a gas-tight seal between the oxygen sensor 10 and the sensor holder. An electrical connector 61 may be mounted to the circuit board 18 for enabling communication of signals between the signal processing module 50 and one or more circuits interfaced with the electrical connector 61 via a communication cable (not shown). These and other features for enabling the use of the oxygen sensor 10 without a cell block in trace oxygen sensing applications, as well as advantages afforded thereby, are described in greater detail in the co-pending and commonly-owned U.S. patent application entitled OXYGEN SENSOR ASSEMBLY AND HOLDER THEREFOR to Steve Broy and Mann Nguyen, Ser. No. 11/124,839, the disclosure of which is hereby incorporated by reference in its entirety.

Figure 5:
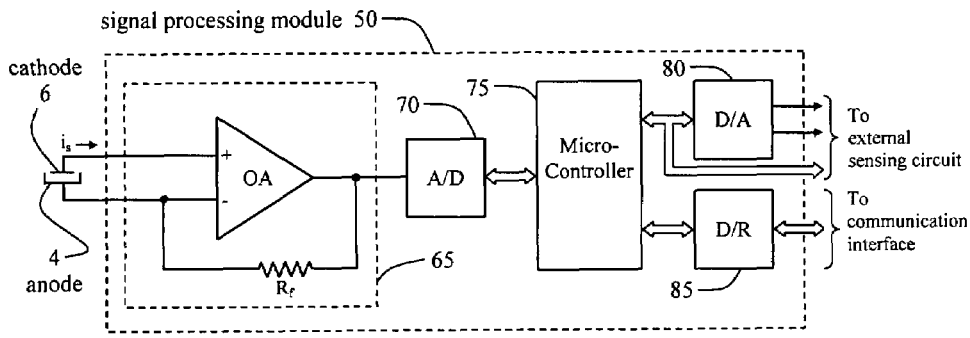
FIG. 5 illustrates a schematic diagram of the signal processing module, according to various embodiments of the present invention.

FIG. 5 illustrates a schematic diagram of the signal processing module 50, according to various embodiments of the present invention. The signal processing module 50 may comprise a current-to-voltage (C/V) converter 65, an analog-to-digital (A/D) converter 70, a microcontroller 75, a digital-to-analog (D/A) converter 80, and a communication driver/receiver (D/R) module 85. According to various embodiments, the signal processing module 50 may further comprise a self-contained power source (not shown) for providing the necessary operating power to components thereof. The power source may comprise, for example, a battery and one or more power distribution and control circuits. According to other embodiments, components of the signal processing module 50 may receive the necessary operating power from a power source (not shown) externally located with respect to the oxygen sensor 10.

The C/V converter 65 may be in communication with the anode 4 and the cathode 6 and configured to receive the current output by the oxygen sensor 10 (represented in FIG. 5 as $i_s$) and to output a DC voltage proportional to the value of the received current. As shown, the C/V converter 65 may be implemented as a single-stage operational amplifier circuit comprising a feedback resistor $R_f$, wherein the DC voltage output by the C/V converter 65 is given by the product of $i_s$ and $R_f$. The value of $R_f$ may be selected such that the DC voltage output by the C/V converter 65 satisfies the voltage input requirements of the A/D converter 70 over the current output range of the oxygen sensor 10. It will be appreciated that the C/V converter 65 may be implemented using other components and/or configurations, such as, for example, one or more resistors connected in series with the anode 4 and the cathode 6 for outputting a suitable DC voltage signal in proportion to the current received therethrough.

The A/D converter 70 may be in communication with the C/V converter 65 and configured to output a signal comprising digital codes representative of values of the DC voltage signal received from the C/V converter 65. According to various embodiments, the A/D converter 70 may be a 19-bit A/D converter such that the base 10 equivalent of the digital codes (i.e., the "count" value) falls within the range of 0-524,897. By way of example, where the input voltage range of the A/D converter 70 is 0-10 VDC, a voltage of 5 VDC input to the A/D converter 70 will result in the output of a digital code having a count value of 262,143. It will be appreciated that the number of bits contained in each digital code output by the A/D converter 70 may be selected so that a suitable number of output codes is used to represent the DC input voltage signal. For example, the A/D converter 70 may instead be implemented as an 8-bit or 10-bit A/D converter having output codes numbering 256 and 1024, respectively.

The microcontroller 75 may be in communication with the A/D converter 70 and configured to receive digital codes output therefrom. The microcontroller 75 may further be configured to output a signal comprising digital codes representative of a calibrated and/or drift-compensated sensed oxygen concentration based on the received digital codes. As discussed below, the digital codes may be communicated to the D/A converter 80 for conversion into an analog signal. Additionally or alternatively, the digital codes may be output directly by the microcontroller 75 and communicated to, for example, an external sensing circuit via electrical contacts or an electrical connector mounted on the circuit board 18, as described above in connection with the embodiments of FIGS. 4a and 4b, respectively. Although not shown for purposes of clarity, the microcontroller 75 may comprise components well known in the microcontroller art such as, for example, a processor, one or more random access memory (RAM) units, one or more erasable programmable read-only memory (EPROM) units, an interrupt controller unit, timer and/or clock units, and a number of general input/output (I/O) ports for receiving and transmitting digital and/or analog signals. According to various embodiments, one or both of the A/D converter 70 and the D/A converter 80, as well as other pictured components of the signal processing module 50, may be integral to the microcontroller 75. According to various embodiments, the microcontroller 75 may be an 87C51FB microcontroller available from the Intel Corporation.

The D/A converter 80 may be in communication with the microcontroller 75 and configured to convert digital codes output therefrom into an analog signal representative of a calibrated and/or drift-compensated sensed oxygen concentration. It will be appreciated that the bit resolution of the D/A converter 80 may be selected based upon, among other things, the number of bits contained in the digital codes output by the microcontroller 75. According to various embodiments, for example, the D/A converter 80 may be an 8-bit D/A converter configured to output an analog voltage signal in a range of 0-10 VDC. According to such embodiments, a one-count increase or decrease in the count value of a received digital code will cause the output analog voltage to increase or decrease, respectively, by approximately 0.04 volts. As discussed hereinbelow in connection with FIG. 10, the analog signal output by the D/A converter 80 may be received by an external sensing circuit of an oxygen analyzer via electrical contacts or an electrical connector mounted on the circuit board 18, as described above in connection with the embodiments of FIGS. 4a and 4b, respectively. It will be appreciated that the signal processing module 50 may further comprise one or more circuits (not shown) configured for transforming the analog signal output from the D/A converter 80 into any of a variety of standard analog voltage or current signals compatible with an external sensing circuit. It will further be appreciated that the D/A converter 80 may not be included in embodiments where an analog output signal is not desired or otherwise necessary. According to such embodiments, the oxygen sensor 10 may be configured such that the digital codes output by the microcontroller 75 are provided as an oxygen sensor 10 output.

The D/R module 85 may be in communication with the microcontroller 75 and configured to enable the exchange of information between the microcontroller 75 and a host (not shown). The host may be externally located with respect to the oxygen sensor 10 and connected to the D/R module 85 via electrical contacts or an electrical connector mounted on the circuit board 18, as described above in connection with the embodiments of FIGS. 4a and 4b, respectively. Examples of information that may be supplied to the microcontroller 75 from the host include program instructions to be performed by the microcontroller 75 and data to be stored therein. Examples of information supplied to the host by the microcontroller 75 include digital codes output by the A/D converter 70 and the microprocessor 75, and data relating to the operational status of the microcontroller 75. The D/R module 85 may be configured to use any known signaling protocol, such as, for example, the RS-232 or RS-485 signaling protocols, for implementing the exchange of information.

Figure 6:
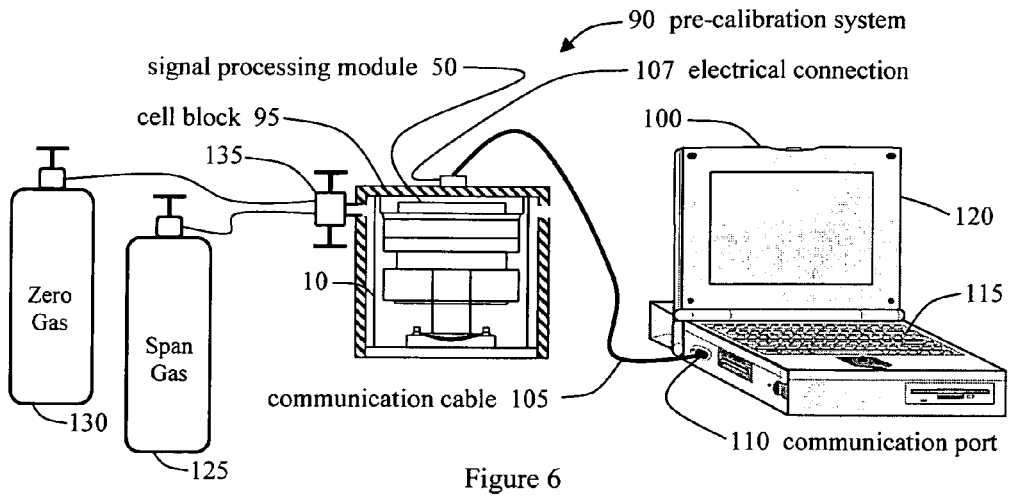
FIGS. 6 and 7 illustrate a system and corresponding method, respectively, for pre-calibrating the oxygen sensor, according to various embodiments of the present invention.
Figure 7:
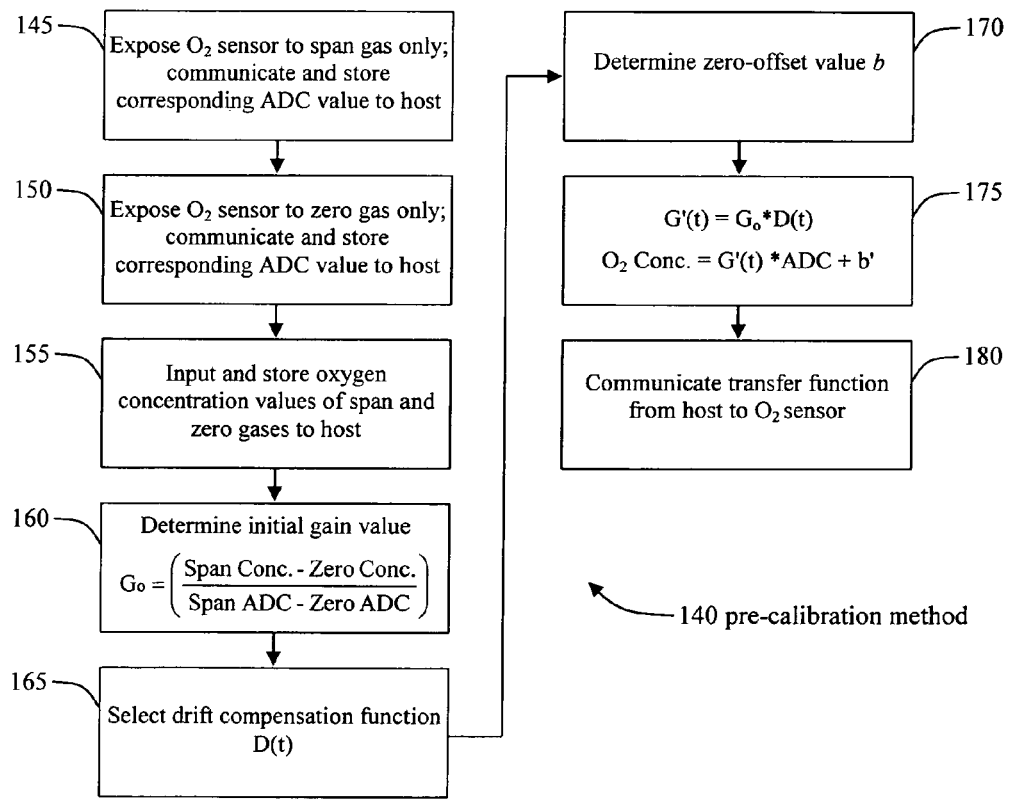

FIGS. 6 and 7 illustrate a system 90 and corresponding method, respectively, for pre-calibrating the oxygen sensor 10 of FIG. 4a, according to various embodiments. It will be appreciated that the system and method of FIGS. 6 and 7 may be modified as necessary for accommodating embodiments of the oxygen sensor 10 shown in FIG. 4b. As used herein, the terms "pre-calibration" and "pre-calibrated" refer generally to a process performed at a location other than the oxygen sensor's 10 point of use wherein the signal processing module 50 of the oxygen sensor 10 is configured to output a calibrated and/or drift-compensated signal representative of a sensed oxygen concentration. According to various embodiments, for example, pre-calibration of the oxygen sensor 10 may be performed at its location of manufacture prior to its delivery and installation at the point of use. Pre-calibration of the oxygen sensor 10 in this manner typically makes any subsequent calibration unnecessary and thus provides significant cost and safety benefits by eliminating the need for procuring, maintaining, and handling calibration gases at the point of use. As discussed below in connection with FIG. 10, pre-calibration of the oxygen sensor 10 may be overridden at the point of use if necessary or otherwise desired.

As shown in the system 90 of FIG. 6, the oxygen sensor 10 may be oriented in the cavity portion of a cell block 95 and in communication with a host 100 via a multiconductor communication cable 105. In particular, a first end of the communication cable 105 may be configured to electrically and mechanically engage a hermetic electrical connection 107 of the cell block 95, and a second end of the communication cable 105 may be configured to electrically and mechanically engage a first communication port 110 of the host 100.

According to various embodiments, the host 100 may be any system capable of exchanging information with the signal processing module 50 of the oxygen sensor 10, such as, for example, a personal computer. The host 100 may include an input device 115, such as a keyboard, and a display 120, such as a computer screen or monitor. The input device 115 may be employed to input information in addition to, or as a substitute for, information that could be provided by the signal processing module 50. The input device 115 allows a user of the host 100 to manually input information therein for use, such as for display or for processing by the host 100. When present, the display 120 may be any device suitable for displaying information, such as that exchanged by the host 100 and the signal processing module 50. Suitable devices may include, for example, light-emitting diodes (LEDs), LED pixel displays, liquid crystal displays (LCDs), raster displays, neon digit displays, and electronic ink.

The first communication port 110 of the host 100 may be any port configured for exchanging information with the signal processing module 50 via the communication cable 105. According to various embodiments, for example, the first communication port 110 may be a serial port configured for exchanging information using the RS-232 or RS-485 signaling protocols. The host system 100 may further comprise a second communication port (not shown) for connecting to the Internet in order to retrieve or transmit information, such as, for example, from or to a website associated with the oxygen sensor's 10 manufacturer. The connection to the Internet may be made either automatically or upon request by the user.

As further shown in FIG. 6, the cavity portion of the cell block 95 may be sealably coupled to a span gas supply 125 and a zero gas supply 130 via a manifold assembly 135. The configuration of the manifold assembly 135 may be such that the oxygen sensor 10 may be separately exposed to the contents of the span and zero gas supplies 125, 130 by appropriately operating control valves integral to the manifold assembly 135. The span gas supply 125 may contain any gas having a substantially non-zero oxygen concentration (e.g., 100 PPM $O_2$, balance $N_2$), and the zero gas supply 130 may contain any gas having an oxygen concentration of zero, or substantially zero (e.g., 100% $N_2$). It will be appreciated that the oxygen concentration of the span gas supply 125 may be selected based upon, among other things, the range of oxygen concentration to be sensed by the oxygen sensor 10.

Figure 2:
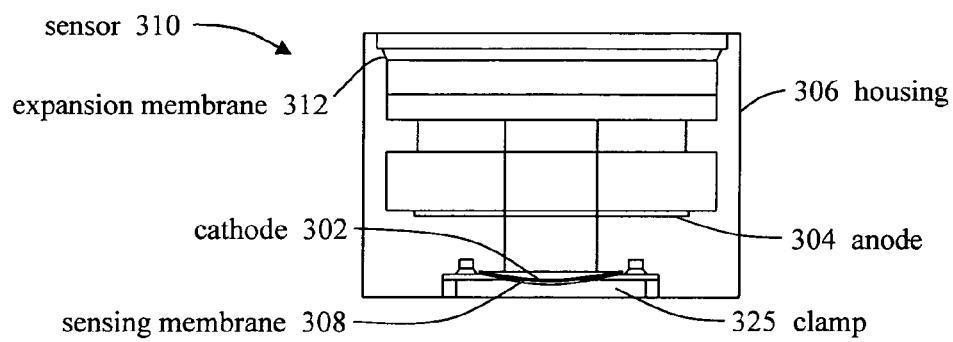
FIG. 2 illustrates a cross-sectional view of the conventional oxygen sensor of FIG. 1 sealed by a clamp portion.
Figure 3:
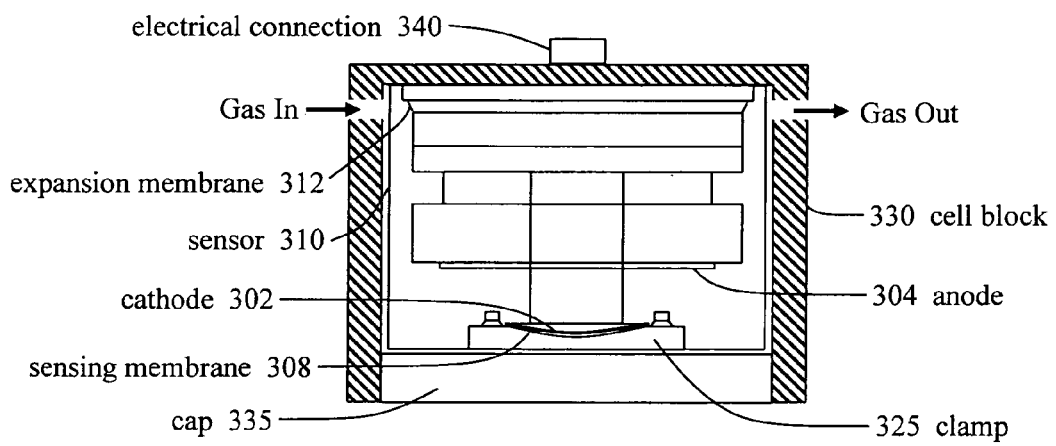
FIG. 3 illustrates a cross-sectional view of the oxygen sensor of FIG. 2 oriented within a cavity portion of a cell block.

As discussed above in connection with the conventional oxygen sensor 310 of FIGS. 1-3, a transfer function of the form $G^*i_s+b$ may be derived for expressing the sensed oxygen concentration as a function of the oxygen sensor's 310 current output, $i_s$. An analogous pre-calibration transfer function may be derived for the oxygen sensor 10 of the present invention by substituting digital codes output by the A/D converter 70 in place of the current output. The pre-calibration transfer function for the oxygen sensor 10, according to various embodiments, may thus be expressed as $O_2$ Conc., cal.=G'(t)*ADC+b', where G'(t) represents the gain of the oxygen sensor 10 in units of oxygen concentration per digital code count value, ADC represents the count value of the digital code output by the A/D converter 70, and b' represents the zero-offset of the oxygen sensor 10 in units of oxygen concentration. According to such embodiments, the oxygen sensor gain G'(t) may be a time-dependent function and, as discussed in further detail below in connection with FIG. 7, may be modeled as the product of an initial gain constant $G_o$ and a time-dependent drift compensation function D(t).

FIG. 7 illustrates a process flow diagram 140 showing a method of pre-calibrating the oxygen sensor 10 in accordance with the system 90 of FIG. 6, according to various embodiments. This method may be performed, for example, at the oxygen sensor's 10 point of manufacture or other location prior to delivery and installation of the oxygen sensor 10 at the point of use.

At steps 145 and 150, the oxygen sensor 10 is separately exposed to the contents of the span gas supply 125 and the zero gas supply 130. Exposure of the oxygen sensor 10 in this manner may be accomplished by sequentially operating the control valves of the manifold assembly 135. According to various embodiments and as shown in FIG. 6, the control valves may be configured to be manually operated by a user of the system 90. According to other embodiments, the control valves may be configured for operation by a solenoid or other actuating device. In such embodiments, the control valves may be operated automatically using, for example, a programmable logic controller (PLC) (not shown) in communication with the host 100. During each exposure of the oxygen sensor 10 at steps 145 and 150, an ADC value output by the A/D converter 70 is received by the microcontroller 75 and communicated to the host 100. These values are then stored by the host 100 for subsequent processing.

At step 155, the host 100 prompts the user to input the oxygen concentration values corresponding to the span and zero gas supplies 125, 130 via the input device 115. These values are then stored by the host 100 for subsequent processing.

At step 160, the initial gain constant $G_o$ is determined by the host 100 as the ratio $$\frac{\text{Span Conc.} - \text{Zero Conc.}}{ADC, \text{Span} - ADC, \text{Zero}},$$

where the numerator represents the difference in oxygen concentration between the span and zero gas supplies 125, 130 stored at step 155, and the denominator represents the difference between the span and zero ADC values stored at steps 145 and 150, respectively. This value is then stored by the host 100 for subsequent processing.

At step 165, a time-dependent drift compensation function D(t) for the oxygen sensor 10 is selected. According to various embodiments, the drift compensation function for the oxygen sensor 10 may be determined a priori by exposing a representative oxygen sensor of an identical make and/or model to a constant oxygen concentration for a period of time and modeling the time-dependent change in recorded values of oxygen concentration. It will be appreciated that in certain embodiments of the present invention, the selection of a time-dependent drift compensation function may not be necessary or otherwise desirable. For example, in percent-level oxygen sensing applications in which the effects of drift are typically negligible, G'(t) may be suitably approximated by the initial gain constant $G_o$. For such embodiments, the pre-calibration transfer function may thus be expressed as $O_2 Conc. = G_o * ADC + b'$.

Figure 8:
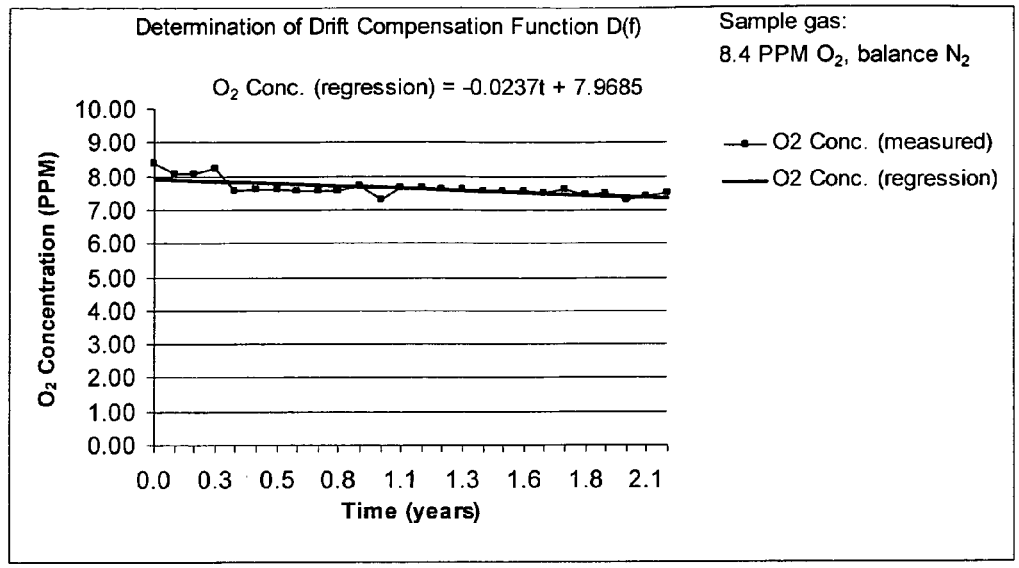
FIG. 8 illustrates an example of a determination of the drift compensation function D(t) for a representative oxygen sensor, according to various embodiments of the present invention.

FIG. 8 illustrates an example of a determination of the drift compensation function D(t) for a representative oxygen sensor, according to various embodiments. The oxygen sensor may be calibrated using conventional calibration methods as described above in connection with the oxygen sensor 310 of FIGS. 1-3. The oxygen sensor may then be exposed to a constant oxygen concentration for a period of time during which the indicated oxygen concentration values are recorded. For example, the oxygen sensor may be exposed to an oxygen concentration of 8.4 PPM over a period of approximately two years. As shown in FIG. 8, the recorded values generally decrease with time due to drift and may be modeled using known curve-fitting techniques. For example, application of a linear regression model to the recorded oxygen concentration values of FIG. 8 yields an oxygen concentration versus time characteristic given by −0.0237*t+7.9685, with the time coefficient being indicative of the rate of decline of the oxygen sensor's gain in units of oxygen concentration per unit time. Based upon the oxygen concentration versus time characteristic derived using the linear regression model, a drift compensation function of the form D(t)=1+0.0237*t may thus be defined such that the product of D(t) and the initial gain value $G_o$ determined at step 160 provides a drift-compensated gain value G'(t) that increases with time such that the effects of sensor drift are minimized.

It will be appreciated that the above-described method for deriving the drift compensation function D(t) for a representative oxygen sensor is provided by way of example only, and that the method may be varied as necessary in accordance with other embodiments. For example, it is contemplated that mathematical models other than linear regression models, such as, for example, polynomial models, logarithmic models, and exponential models, may instead be used to model the oxygen concentration versus time characteristic for the recorded values of oxygen concentration. Other variations may include, for example, variations in the oxygen concentration to which the oxygen sensor is exposed and the time period of its exposure. It is further contemplated that the drift function may be dependent upon one or more quantities in addition to, or other than, time. Such quantities may include, for example, the value of the current output by the oxygen sensor integrated over time, and oxygen concentrations to which the oxygen sensor is exposed.

Referring again to FIG. 7, at step 170 the zero-offset value b' is determined by solving the pre-calibration transfer function $O_2$ Conc., cal.=G'(t)*ADC+b' for b' using the ADC value stored at step 150 and the corresponding oxygen concentration value for the zero gas supply 130 stored at step 155. Accordingly, the value of b' is given as Zero Conc.−G'(t)*(Zero ADC) and may be expressed in units of oxygen concentration. For purposes of this determination, G'(t) may be suitably approximated as the initial gain constant $G_o$.

At step 175, the host 100 compiles the pre-calibration transfer function into a form suitable for communication to the signal processing module 50 of the oxygen sensor 10 based on the values of $G_o$ and b' determined at steps 160 and 170, respectively, and the drift compensation function D(t) determined at step 165. At step 180, the pre-calibration transfer function is communicated from the host 100 to the microcontroller 75 for storage therein.

Figure 9:
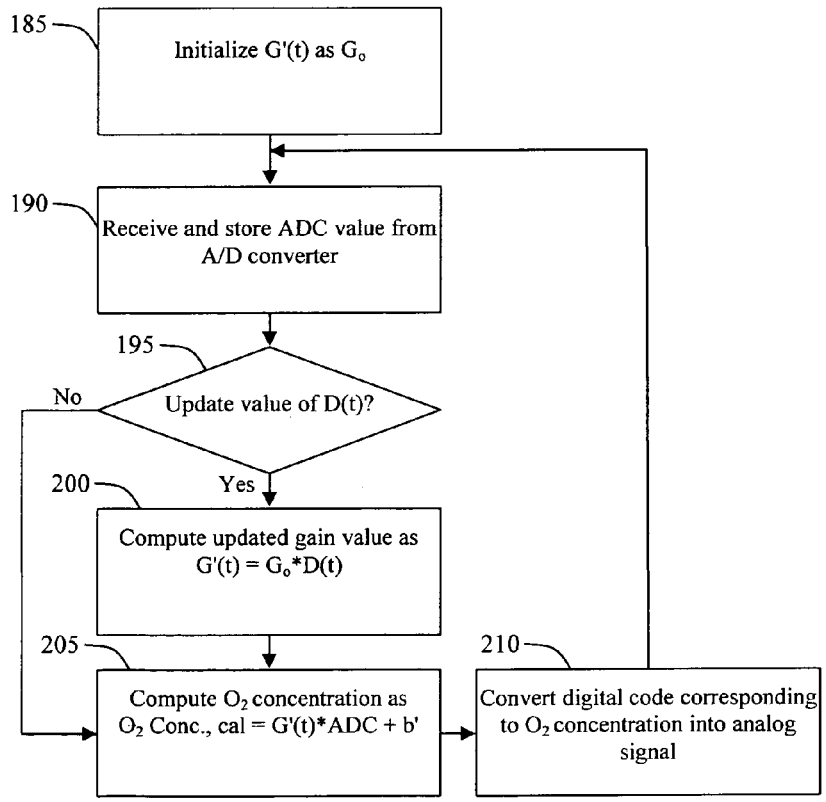
FIG. 9 illustrates a flow diagram of an iterative process executed by the signal processing module for outputting a calibrated and drift-compensated signal representative of a sensed oxygen concentration, according to various embodiments of the present invention.

FIG. 9 illustrates a flow diagram of an iterative process executed by the signal processing module 50 for outputting a calibrated and drift-compensated signal representative of a sensed oxygen concentration, according to various embodiments of the present invention. According to such embodiments, the process may be executed by the signal processing module 50 after pre-calibration of the oxygen sensor 10 in accordance with the method of FIG. 7 and after oxygen sensor 10 has been installed at the point of use.

Beginning at step 185, the microcontroller 75 initializes the value of the oxygen sensor's gain G'(t) as $G_o$.

At step 190, the microcontroller 75 receives and stores an ADC value from the A/D converter 70 that is representative of the value of the DC voltage signal output by the C/V converter 65.

At step 195, the microcontroller 75 determines whether the value of G'(t) is to be updated. According to various embodiments, the microcontroller 75 may perform this determination based upon a time value indicated by an internally-maintained time reference, such as a time-based counter or clock. According to such embodiments, the microcontroller 75 may be configured to update the value of G'(t) at each expiration of a predetermined time interval (e.g., hourly, daily, monthly). If an expiration of the predetermined time interval is detected at step 195, the process proceeds to step 200 wherein an updated value of the gain G'(t) is determined and the pre-calibration transfer function updated and stored accordingly. From step 200, the process proceeds to step 205. If an expiration of the predetermined time interval is not detected at step 195, the current value of G'(t) is retained and the process proceeds to step 205.

At step 205, a value of the calibrated and drift-compensated oxygen concentration is determined by the microcontroller 75 by substituting into the stored pre-calibration transfer function the ADC count value stored at step 190. A digital code corresponding to the determined value of oxygen concentration is then output to the D/A converter 80. Additionally, the digital code may be directly provided as an oxygen sensor 10 output.

At step 210, the D/A converter 80 converts the received digital code into an analog signal such as, for example, a 0-10 VDC analog signal, that is representative of the calibrated and drift-compensated oxygen concentration value determined by the microcontroller 75. From step 210, the process returns to step 190, and the process is repeated in an iterative manner. It will be appreciated that in embodiments not including a D/A converter 80, step 210 may be omitted and the digital code output by the microcontroller 75 at step 205 directly provided as an oxygen sensor 10 output.

Figure 10:
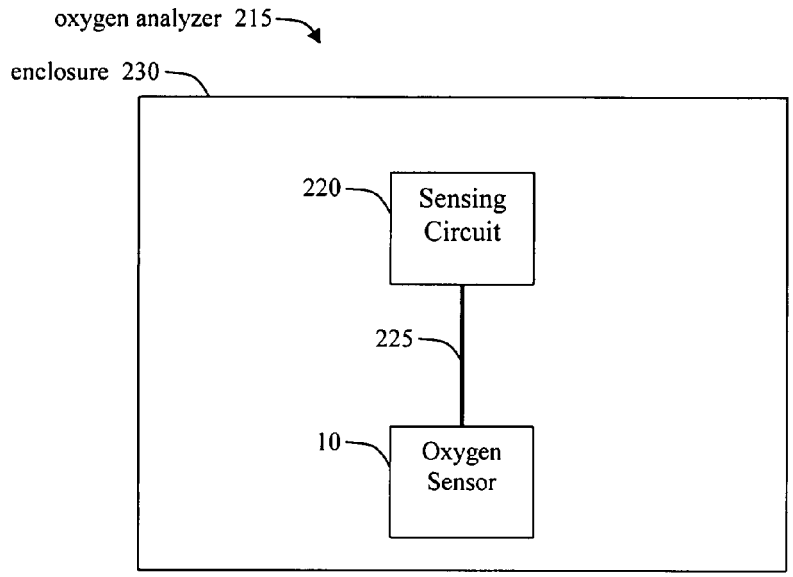
FIG. 10 illustrates a schematic diagram of an oxygen analyzer comprising the oxygen sensor subsequent to its pre-calibration in accordance with the method of FIG. 7, according to various embodiments of the present invention.

FIG. 10 illustrates a schematic diagram of an oxygen analyzer 215 comprising the oxygen sensor 10 subsequent to its pre-calibration in accordance with the method of FIG. 7, according to various embodiments of the present invention. The oxygen analyzer 215 may further comprise an external sensing circuit 220 for receiving digital codes output by the microcontroller 75 and/or the analog signal output by the D/A converter 80 via a conductor pair 225, and an enclosure 230 housing the oxygen sensor 10, the external sensing circuit 220, and the conductor pair 225.

The external sensing circuit 220 may be any known sensing circuit for converting digital codes output by the microcontroller 75 and/or the analog signal output by the D/A converter 80 into an oxygen concentration output. According to various embodiments, the external sensing circuit 220 may include one or more microprocessors, signal processors, power supplies, data input devices, and display devices for implementing the conversion and for outputting the corresponding result. Additionally, the external sensing circuit 220 may include communication capabilities similar or identical to those of the host 100 for enabling the exchange of information between the external sensing circuit 220 and the signal processing module 50 in the manner similar to that described above with respect to FIGS. 6 and 7. Accordingly, if necessary or otherwise desired, the pre-calibration of the oxygen sensor 10 may be overridden and a new transfer function communicated thereto.

The enclosure 230 may be any type of known enclosure suitable for housing the oxygen sensor 10, external sensing circuit 220, and conductor pair 225 and for accommodating process lines and control valves necessary for the delivery and exhaust of the sample gas stream. Although the oxygen sensor 10 is shown in FIG. 10 as being contained within the enclosure 230, it will be appreciated that in other embodiments the oxygen sensor 10 may be externally located with respect to the enclosure 230.

Figure 11:
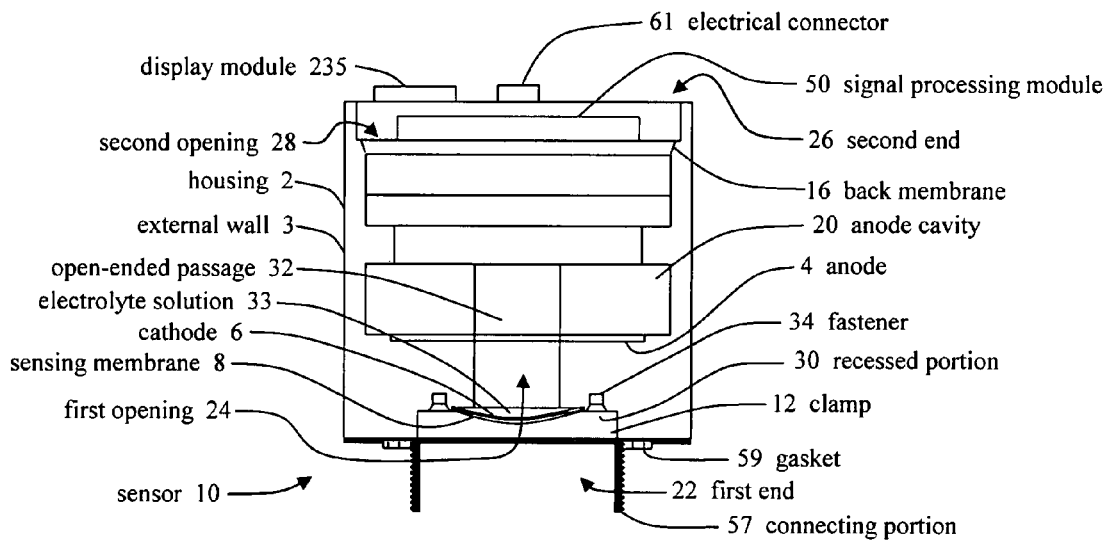
FIG. 11 illustrates a cross-sectional view of an oxygen sensor, according to various embodiments of the present invention.

According to various embodiments, the oxygen sensor 10 may be configured for use without an oxygen analyzer. As shown in FIG. 11, for example, embodiments of oxygen sensor 10 may be configured for use as a standalone device and further comprise a display module 235 including for example, an LCD display, integral to the oxygen sensor 10. The display module 235 may be in communication with the signal processing module 50 and configured to display oxygen concentration readings based on at least one of the analog signal output by the D/A converter 80 and the digital codes output by the microcontroller 75. Although the incorporation of the display 235 enables the use of the oxygen sensor 10 as a standalone device, it will be appreciated that the analog signal and/or digital codes output by the oxygen sensor 10 may also be simultaneously communicated to external sensing circuits (e.g., oxygen analyzers, process controllers).

Whereas particular embodiments of the invention have been described herein for the purpose of illustrating the invention and not for the purpose of limiting the same, it will be appreciated by those of ordinary skill in the art that numerous variations of the details, materials, configurations and arrangement of components may be made within the principle and scope of the invention without departing from the spirit of the invention. The preceding description, therefore, is not meant to limit the scope of the invention.

The invention claimed is:

1. A pre-calibrated gas sensor, comprising:
   a cathode and an anode for outputting a current signal responsive to a sensed oxygen concentration, wherein the cathode and the anode are in communication with a liquid electrolyte solution; and
   a signal processing module in communication with the cathode and the anode and having a pre-calibration transfer function stored therein, wherein the signal processing module comprises a microcontroller and is configured to receive the current signal and to output a pre-calibrated signal representative of the sensed oxygen concentration based on the pre-calibration transfer function and a value of the received current signal, and wherein the pre-calibration transfer function comprises a gain function for compensating a time-dependent drift of the gas sensor caused by at least one of a reduction in ion concentration of the electrolyte solution and formation of precipitates on the anode.

2. The gas sensor of claim 1, further comprising a housing enclosing the cathode, the anode, and the signal processing module.

3. The gas sensor of claim 1, wherein the signal processing module is further configured to receive the pre-calibration transfer function from a host computer in communication therewith.

4. The gas sensor of claim 1, wherein the gain function comprises an initial gain constant and a drift compensation function having time as an independent variable.

5. The gas sensor of claim 1, wherein the signal processing module further comprises an analog-to digital (A/D) converter in communication with the microcontroller.

6. The gas sensor of claim 1, wherein the signal processing module further comprises a digital-to-analog (D/A) converter in communication with the microcontroller.

7. The gas sensor of claim 1, wherein the signal processing module further comprises a communication driver/receiver (D/R) module in communication with the microcontroller.

8. The gas sensor of claim 1, further comprising a display module in communication the signal processing module.

9. The gas sensor of claim 5, wherein the signal processing module further comprises a current-to-voltage (C/V) converter in communication with the A/D converter.

10. A system for pre-calibrating a gas sensor, comprising:
    a cathode and an anode for outputting a first current signal responsive to a sensed oxygen concentration in a first gas, wherein the cathode and the anode are in communication with a liquid electrolyte solution;
    a signal processing module in communication with the cathode and the anode, wherein the signal processing module comprises a microcontroller and is configured to receive the first current signal and to output a first digital code representative of the first current signal; and
    a host computer in communication with the signal processing module, wherein the host computer is configured to receive the first digital code and to determine a pre-calibration transfer function based on the first digital code and a time-dependent drift of the gas sensor caused by at least one of a reduction in ion concentration of the electrolyte solution and formation of precipitates on the anode.

11. The system of claim 10, further comprising a housing enclosing the cathode, the anode, and the signal processing module.

12. The gas sensor of claim 10, wherein the cathode and the anode are further for outputting a second current signal responsive to a sensed oxygen concentration in a second gas, wherein the signal processing module is further configured to receive the second current signal and to output a second digital code representative of the second current signal, and wherein the host computer is further configured to receive the second digital code and to determine the pre-calibration transfer function based thereon.

13. The system of claim 10, wherein the host computer is further configured to communicate the determined pre-calibration transfer function to the signal processing module for storage therein.

14. The system of claim 12, wherein the first gas is a span gas and the second gas is a zero gas.

* * * * *

UNITED STATES PATENT AND TRADEMARK OFFICE
CERTIFICATE OF CORRECTION

PATENT NO. : 7,664,607 B2 Page 1 of 1
APPLICATION NO. : 11/243042
DATED : February 16, 2010
INVENTOR(S) : Stephen H. Broy It is certified that error appears in the above-identified patent and that said Letters Patent is hereby corrected as shown below:

On the Title Page, Item (73) ASSIGNEE:

Delete "Los Angeles, CA (US)" and replace therewith --Thousand Oaks, CA (US)--.

Signed and Sealed this

Sixth Day of July, 2010

David J. Kappos
*Director of the United States Patent and Trademark Office*